United States Patent [19]
Davis et al.

[11] Patent Number: 6,069,235
[45] Date of Patent: May 30, 2000

[54] METHOD FOR CARBOHYDRATE ENGINEERING OF GLYCOPROTEINS

[75] Inventors: Simon J. Davis; Terence D. Butters, both of Oxford, United Kingdom; Gunilla B. Karlsson, Boston, Mass.; Frances M. Platt, Oxford, United Kingdom; Martin L. Bryant, Chesterfield, Mo.; Raymond A. Dwek, Oxford, United Kingdom

[73] Assignee: Monsanto Company, St. Louis, Mo.

[21] Appl. No.: 08/202,055

[22] Filed: Feb. 23, 1994

[51] Int. Cl.$^7$ ....................................................... C07K 1/113
[52] U.S. Cl. ............................................ 530/402; 530/395
[58] Field of Search ........................... 435/41, 68.1, 69.2, 435/70.1, 85; 530/395, 69, 240.1, 402

[56] References Cited

U.S. PATENT DOCUMENTS

| | | | |
|---|---|---|---|
| 4,925,796 | 5/1990 | Bergh et al. | 435/97 |
| 5,021,427 | 6/1991 | Elbein et al. | 435/119 |

FOREIGN PATENT DOCUMENTS

| | | | |
|---|---|---|---|
| WO 89/07641 | 8/1989 | WIPO | A61K 37/02 |

OTHER PUBLICATIONS

Karlsson et al; J. Biol. Chem., 268, 570–576 (1993).
Davis et al; Protein Eng. 6, 229–32 (1993).
Hiraizumi et al; J. Biol. Chem. 268, 9927–9935 (1993).
Platt et al; Eur. J. Biochem. 208, 187–193 (1992).
Davis et al. J. Biol. Chem. 270, 369–375 (1995).
Chem. Abstracts, vol. 116, No. 21, #209747.
Chan et al. 1992. Mol. Biol. Cell 3: 157–166.
Jones et al. 1992. Nature 360:232–239.
Peyrieras et al. 1983. EMBO J2: 823–832.
Platt et al. 1992. Eur. J. Biochem. 208:187–193.
Romero et al. 1986. J. Biol. Chem. 261:15936–15940.

*Primary Examiner*—Elizabeth Kemmerer
*Attorney, Agent, or Firm*—Scott J. Meyer

[57] ABSTRACT

A method is disclosed for modifying the carbohydrate moiety on glycoproteins to facilitate the structural and functional analysis of said glycoproteins such as by NMR spectroscopic analysis and crystallography which comprises treating glycoprotein-secreting mammalian cells having low endomannosidase activity under cell culture maintenance conditions with a glucosidase I inhibitor, and after secretion and purification, subsequent treatment of the active glycoprotein with endoglycosidase H to thereby provide a glycoprotein with a single GlcNAc residue at each glycosylation sequon. The preferred mammalian cells are CHO cells and the preferred glucosidase I inhibitor is N-butyl deoxynojirimycin.

3 Claims, 16 Drawing Sheets

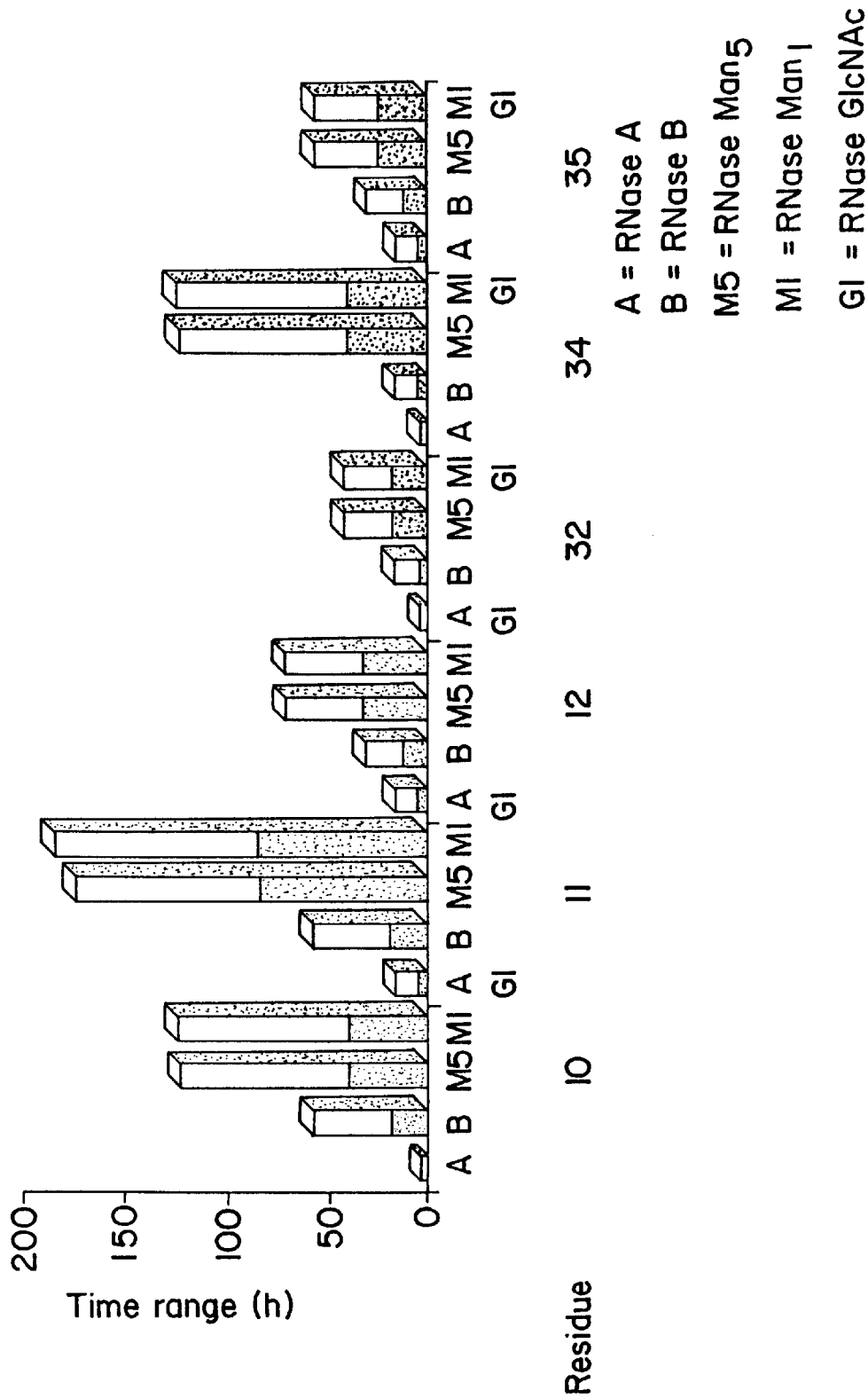

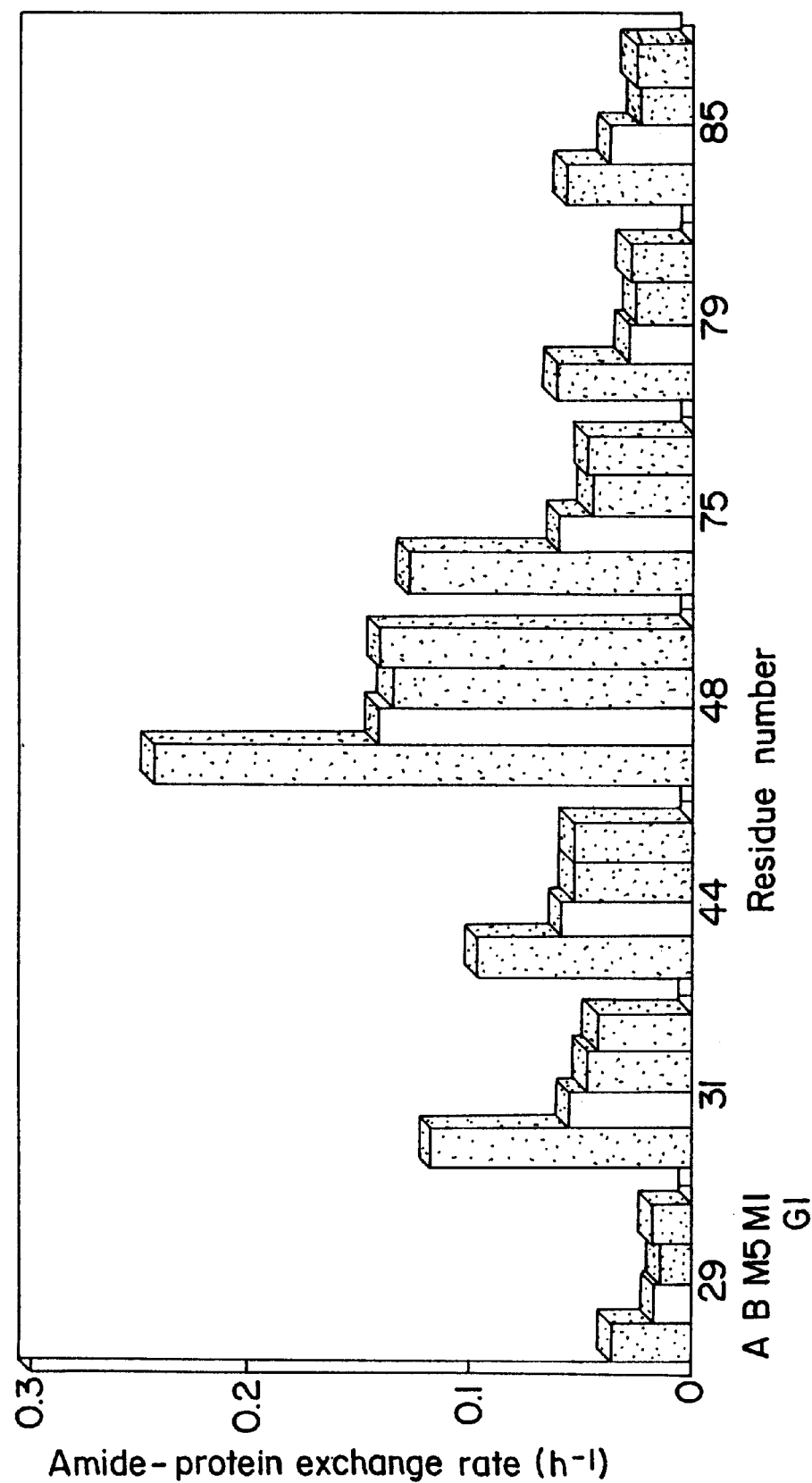

6,069,235

METHOD FOR CARBOHYDRATE ENGINEERING OF GLYCOPROTEINS

BACKGROUND OF THE INVENTION

This invention relates to a method of carbohydrate engineering of glycoproteins. More particularly, the present invention concerns a method of modifying the carbohydrate moiety on mammalian cell-secreted glycoproteins to facilitate the structural and functional analysis of the secreted glycoproteins.

A large number of proteins of key scientific and medical interest are heavily glycosylated. In many cases the carbohydrate accounts for 50% of the molecular weight of the glycoprotein. This can present serious obstacles to the structural analysis of these molecules by crystallographic and NMR-based procedures. As discussed previously (Davis et al., 1993), the oligosaccharides may obscure the protein surface, or oligosaccharide microheterogeneity (the presence of multiple glycoforms) may prevent the formation of reproducible crystal contacts involving the oligosaccharides directly. Alternatively, if the oligosaccharides are able to form crystal contacts, the flexibility and mobility of the oligosaccharides may limit the order of the crystals. In the case of NMR analyses, heavy glycosylation may increase spectral complexity, exacerbate peak broadening due to increased molecular weight, or impose peak microheterogeneity as a result of variation in the length and composition of the oligosaccharides present on each of the glycoforms.

Although a detailed survey has not been published, in the experience of the present inventors the removal of complex oligosaccharides from glycoproteins is generally difficult. Several approaches for preventing the addition of oligosaccharides or for facilitating their removal may be successful in individual cases; however, each of these approaches has significant limitations so that general solutions to the problem of glycosylation have been elusive (discussed in Davis et al., 1993). The ideal strategy is one that allows (1) the normal transfer of the $Glc_3Man_9GlcNAc_2$ oligosaccharide precursor to the protein and therefore the correct folding of the glycoprotein in the endoplasmic reticulum of eukaryotic cells and (2) the subsequent inhibition of oligosaccharide processing to complex forms, thus rendering the oligosaccharides endo H-sensitive and allowing their subsequent removal prior to structural analysis.

The effectiveness of such a strategy has been demonstrated by producing the cell adhesion molecule, rat soluble CD2 (sCD2), in a Chinese Hamster ovary (CHO) cell glycosylation mutant, Lec3.2.8.1 (Stanley, 1989), which is largely defective in processing oligosaccharides beyond endo H-sensitive, $Man_5GlcNAc_2$ forms (Davis et-al., 1993). This work led directly to a crystal structure for rat sCD2 (Jones et al., 1992). However, this approach suffers from the drawbacks that the Lec3.2.8.1 cell line is difficult to transfect (Davis et al., 1993) and yields of fully endo H-sensitive glycoforms can in some instances be less than 50% (S. J. Davis, unpublished).

Further background information on the analysis of secreted and membrane-associated glycoproteins can be had by reference to the recent review article by Dwek et al., *Ann. Rev. Biochem.* 62. 65–100 (1993).

BRIEF DESCRIPTION OF THE INVENTION

In accordance with the present invention a method is provided for modifying the carbohydrate moiety on glycoproteins to facilitate the structural and functional analysis of said glycoproteins such as by NMR spectroscopic analysis and crystallography. The method comprises treating glycoprotein-secreting mammalian cells having low endomannosidase activity under cell culture maintenance conditions with a glucosidase I inhibitor, and after secretion and purification, subsequent treatment of the active glycoprotein with endoglycosidase H (endo H) to provide a glycoprotein with a single GlcNAc residue at each glycosylation sequon and to thereby facilitate structural and functional analysis of said secreted glycoprotein.

Preferred cell culture maintenance conditions comprise incubation of the mammalian cells in conventional nutrient culture medium at 35–37° C., 5% $CO_2$. Nutrient culture media for the growth of mammalian cells are conventional and available from many commercial sources. An excellent survey on these sources is provided by Helen J. Morton, In Vitro, Vol. 6, No. 2, pp. 89–108 (1970). A conventional MEM (Modified Eagle Medium) supplemented with Fetal Calf Serum (FCS) is illustrative of such useful media.

Chinese hamster ovary (CHO) cell lines are preferably used as the glycoprotein-secreting mammalian cells in the method of the invention. CHO cells are known to possess low levels of endomannosidase activity as reported by Hiraizumi et al., *J. Biol. Chem.* 268. 9927–9935 (1993) and demonstrated in Example 1 herein. It is also known that the addition of the glucosidase I inhibitor, N-butyl deoxynojirimycin (NB-DNJ), to a transfected CHO cell line secreting immunodeficiency virus envelope glycoprotein, gp120, allows production of glycoprotein which is almost completely sensitive to endo H treatment under denaturing conditions. See Karlsson et al., *J. Biol. Chem.* 262, 570–576 (1993).

A preferred CHO cell line is CHO-K1 which is available to the public from the American Type Culture Collection, Rockville, Md., under accession number ATCC CCL 61.

Glucosidase I inhibitors are well known and include, e.g., deoxynojirimycin, castanospermine and derivatives of these compounds and other such amino-sugar derivatives as described, e.g., by Elbein, *Ann. Rev. Biochem.* 56, 497–534 (1987); Elbein, *Meth. Enzymol.* 138, 661–709 (1987); Furhmann et al., *Biochem. Biophys. Acta* 825, 95–110 (1987), and Fleet et al, *FEBS Lett.* 237, 128–132 (1988). Although any of these conventional glucosidase I inhibitors can be used, N-alkyl ($C_1$–$C_8$) derivatives of deoxynojirimycin, e.g. N-butyl deoxynojirimycin, are the preferred glucosidase I inhibitors for use in the method of the invention.

The glucosidase I inhibitor is used at concentrations sufficient to prevent the enzyme breaking down the glycosylated precursor. Effective concentrations are at least about 0.1 mM but generally in the range of 0.5 to 2.0 mM.

In a preferred embodiment of the invention, N-butyl deoxynojirimycin is used in a concentration of about 0.5 to about 2 mM and-endoglycosidase H (endo H) is used at a concentration of from about 4 to about 100 mU/ml. As used herein, one unit (U) of endo H is defined as the enzyme activity which hydrolyzes one micromole ($\mu$M) of dansyl-Asn-(GlcNAc)$_2$-(Man)$_5$ within one minute at 37° C., pH 5.5.

In accordance with a preferred embodiment of the invention, the addition of N-butyl deoxynojirimycin (NB-DNJ) to cultures of a transfected CHO cell line secreting a recombinant form of human soluble CD2 (hsCD2), which has three glycosylation sites, induces the secretion of hsCD2 with oligosaccharides that are sensitive to endo H under non-denaturing conditions. The trimming of these oligosaccharides to single N-acetylglucosamine residues does not compromise its ability to bind antibodies or its ligand CD58(LFA-3), suggesting that the conformation of the protein is retained, but allows the crystallization of hsCD2. Complementary studies of individual glycosylated variants (glycoforms) of the model glycoprotein, bovine pancreatic RNase B, show that the presence of a single GlcNAc residue at the N-glycosylation sequon (Asn 34 Leu Ser) endows the RNase with the same dynamic stability as $Man_5GlcNAc_2$ or larger oligosaccharides and the same resistance to protease as the RNase B-Man5 glycoform. The present work, in agreement with previous X-ray crystallographic analyses of RNase B and the unglycosylated form of the molecule, RNase A, also shows that the 3D-structure of RNase B is independent of the oligosaccharides associated with the enzyme. These results facilitate the structural and functional analysis of glycoproteins.

The method of the invention facilitates the structural and functional analysis of glycoproteins in two unexpected ways, quite apart from the fact that the glycopart would be missing and, thereby, simplify NMR spectra. Thus, the disclosed illustrative, detailed work on ribonuclease with the single sugar residue, GlcNAc, on the molecule shows that it has protease resistance characteristic of more fully glycosylated proteins and that it also has enhanced dynamic stability as probed by hydrogen deuterium exchange on NMR studies. These results have two important corollaries. Firstly, the protease resistance means that long term NMR studies can be undertaken for structure determination with an expectation that the protease resistance, due to the extra single sugar residue, will keep the protein intact to a greater extent than if it were absent. Secondly, the enhanced dynamic stability of the molecule with the single sugar residue will facilitate making a more rigid structure so that in crystallographic determinations the B factors, which are a measure of disorder, will be somewhat reduced, thereby giving a better crystal structure.

Other illustrative glycoproteins which can be secreted from CHO cells and subjected to structural and functional analysis in accordance with the method of the invention are, e.g., gp120, CD4, human CD2, rat CD2, HCD59, OX-45 (MRC), CD5, t-PA, LACI and the like glycoproteins. For example, secretion of tPA from CHO cells is described in U.S. Pat. No. 4,766,075, and secretion of LACI from CHO cells is disclosed in U.S. Pat. No. 5,212,091.

DETAILED DESCRIPTION OF THE INVENTION

Figure 1:
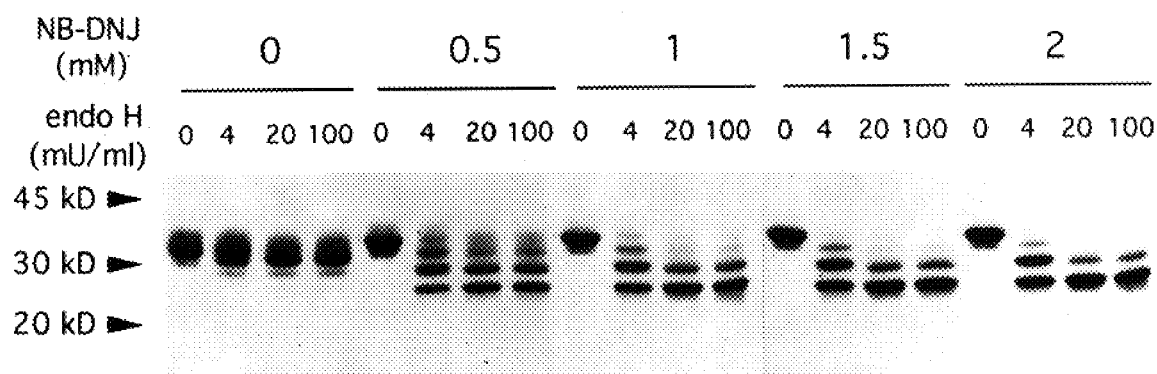

While the specification concludes with claims particularly pointing out and distinctly claiming the subject matter regarded as forming the invention, it is believed that the invention will be better understood from the following illustrative detailed description taken in conjunction with the accompanying drawings in which:

FIG. 1 shows the effect of NB-DNJ on endoglycosidase H sensitivity of hsCD2 oligosaccharides. Human sCD2 was expressed in the presence of 0, 0.5, 1.0, 1.5 or 2 mM NB-DNJ, purified to homogeneity and then digested overnight with endo H at 4, 20 or 100 mU/ml. The digestion products (3 μg) were then electrophoresed with undigested hsCD2 on a 15% SDS-PAGE gel alongside equivalent amounts of the starting material for each digestion. The gel was stained with Coomassie Blue. Molecular weight markers are shown at the left.

Figure 2A:
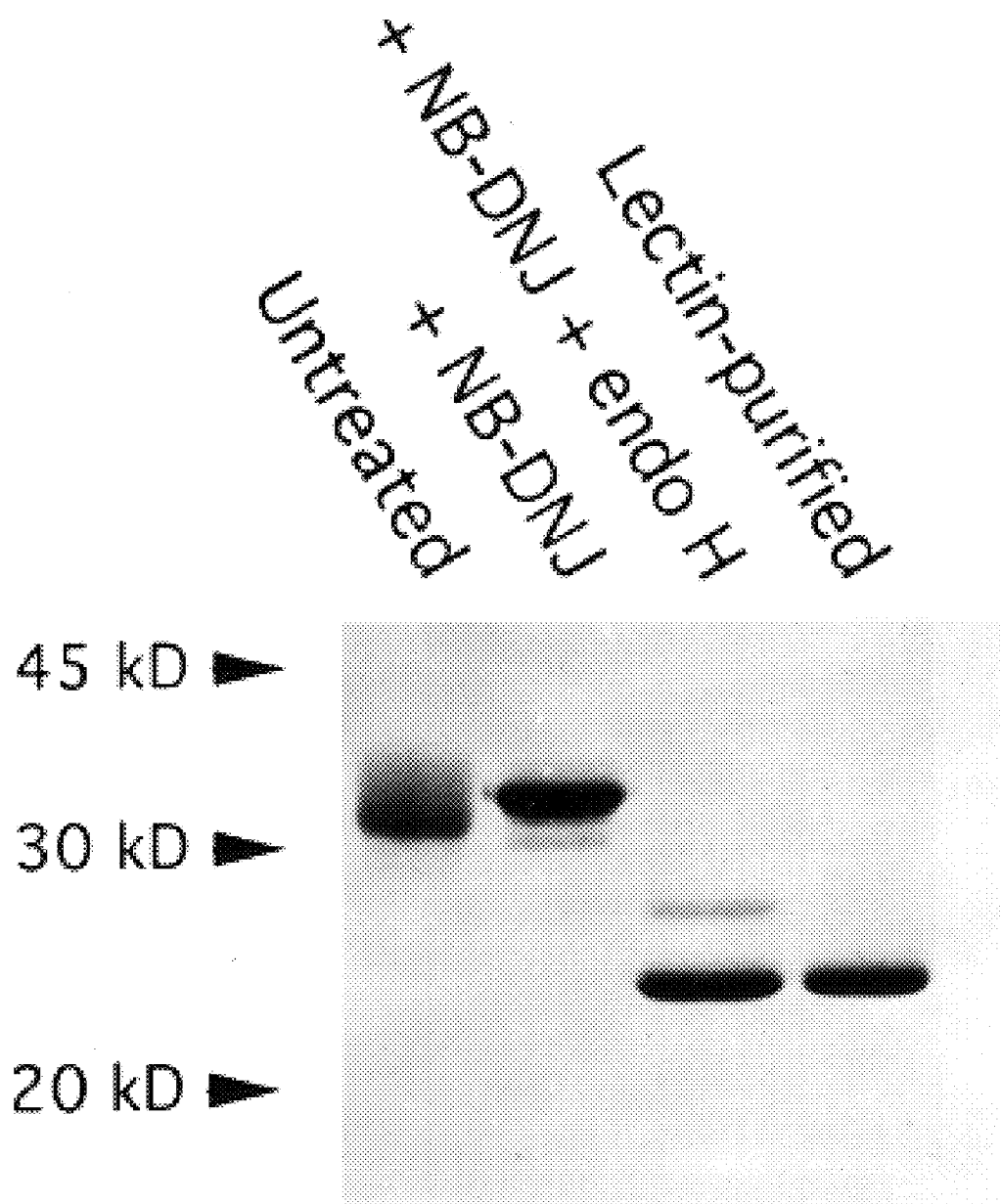

FIG. 2A shows the preparation and purification of endo H treated hsCD2. Human sCD2 was expressed in the absence (lane 1, untreated) or presence (lane 2) of NB-DNJ (1.5–2 mM). The protein prepared in the presence of NB-DNJ was treated with 100 mU/ml endo H (lane 3) prior to final purification by lectin affinity chromatography (lane 4). 5 μg of each protein was electrophoresed on an SDS-PAGE gel and the gel was then stained with Coomassie Blue. Molecular weight markers are shown at the left.

Figure 2B:
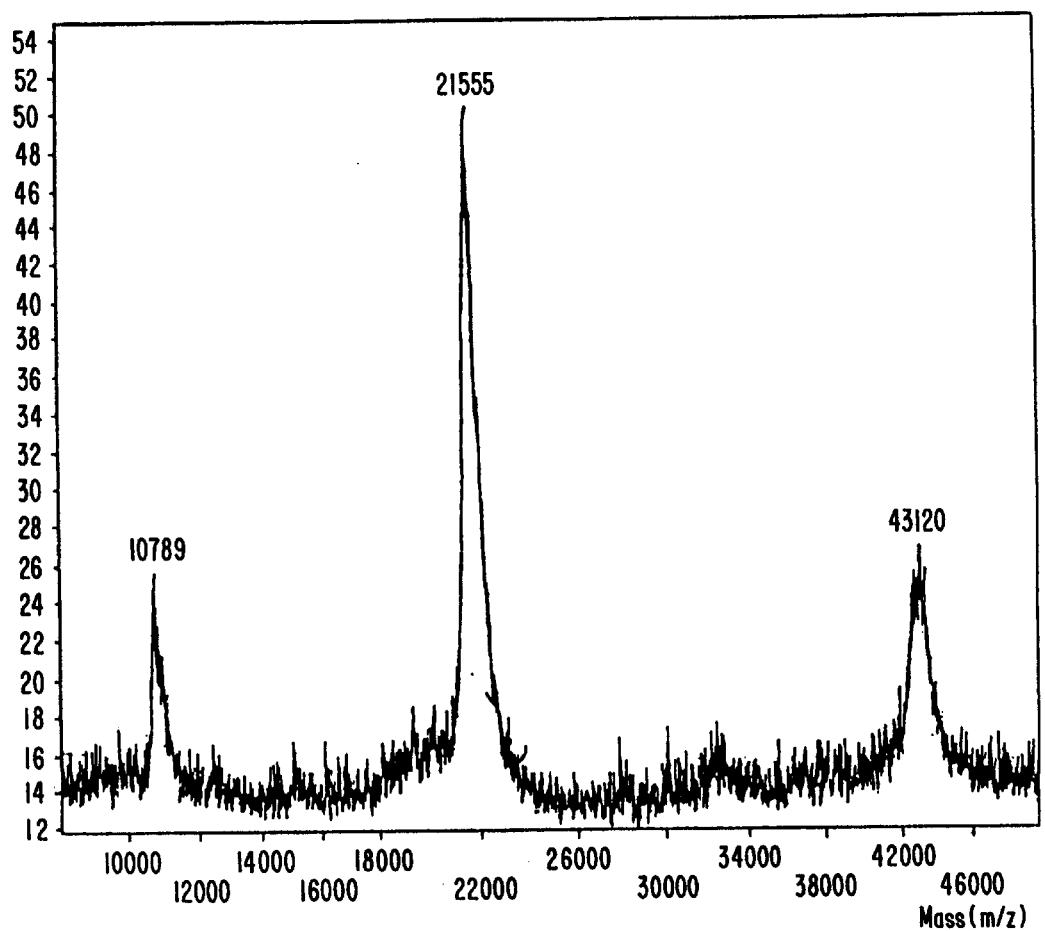

FIG. 2B shows Matrix assisted, laser desorption mass spectrometry which indicates that the molecular weight of the endo H treated lectin-affinity purified hsCD2 is 21555 Da, a value which agrees well with the calculated MW of 21578 for the hsCD2 polypeptide with single GlcNAc residues at each of three N-glycosylation sites.

Figure 3A:
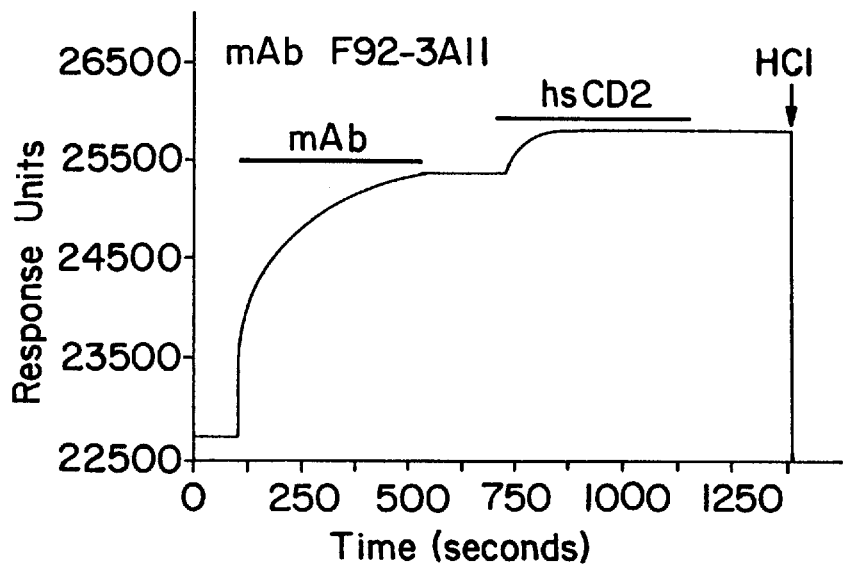
Figure 3B:
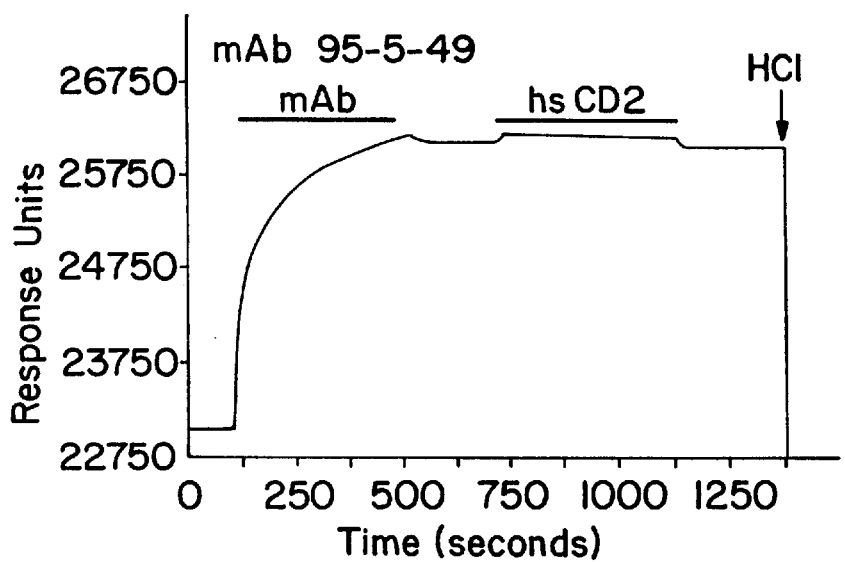
Figure 3C:
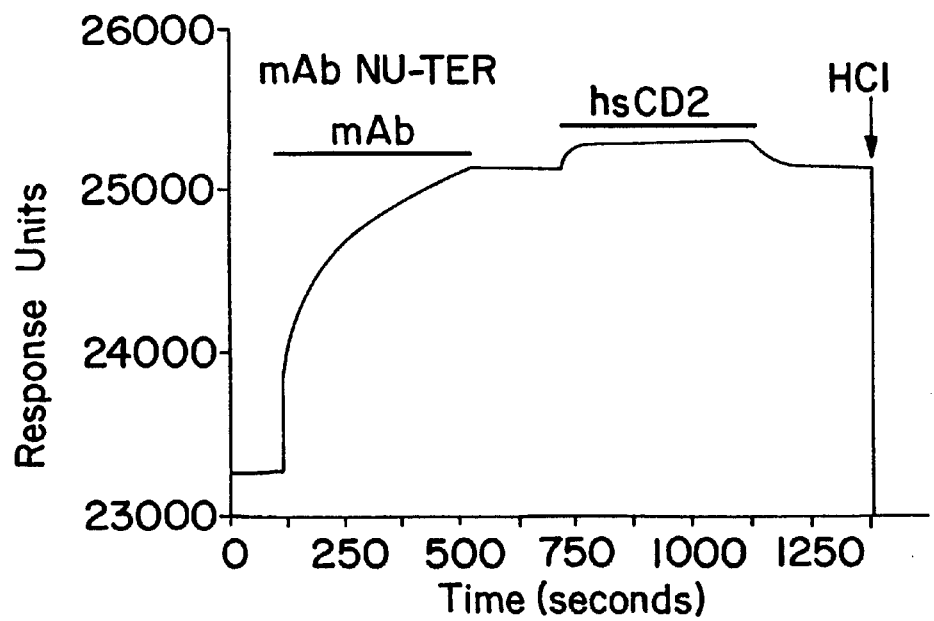
Figure 3D:
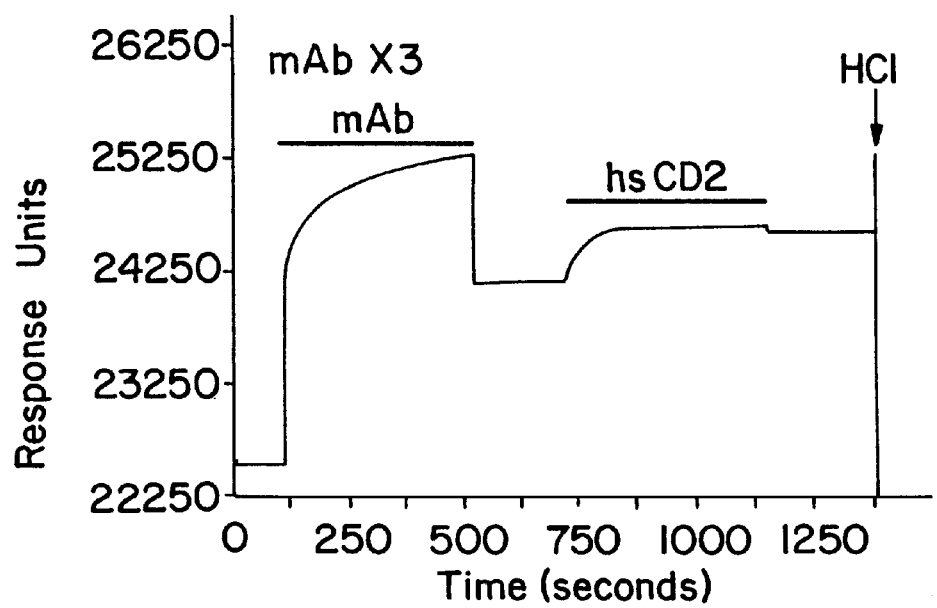
Figure 3E:
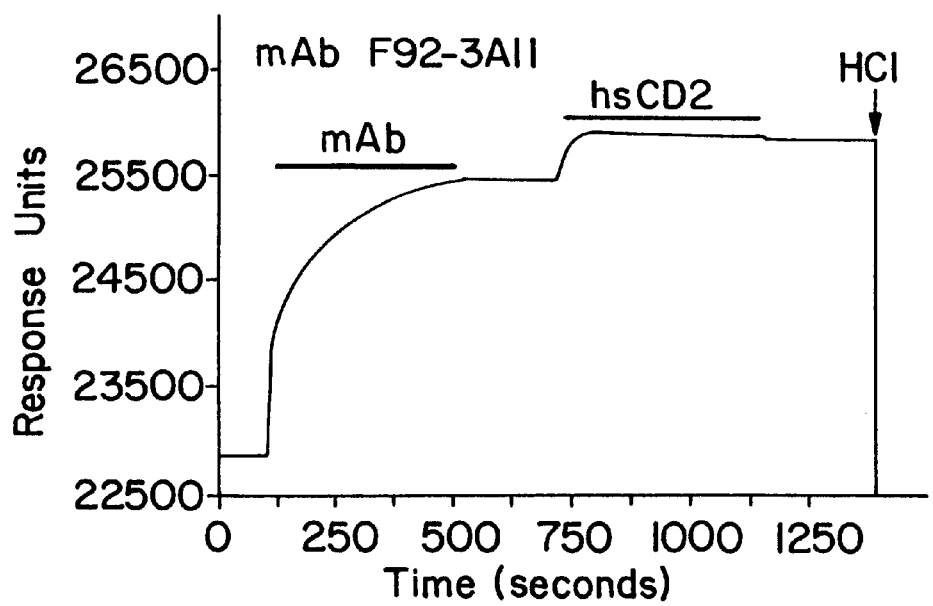
Figure 3F:
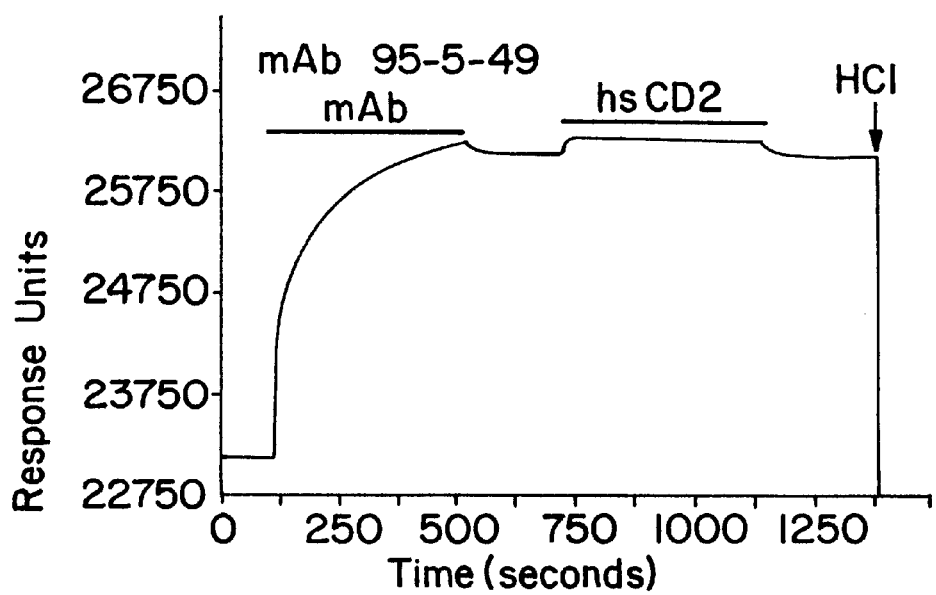
Figure 3G:
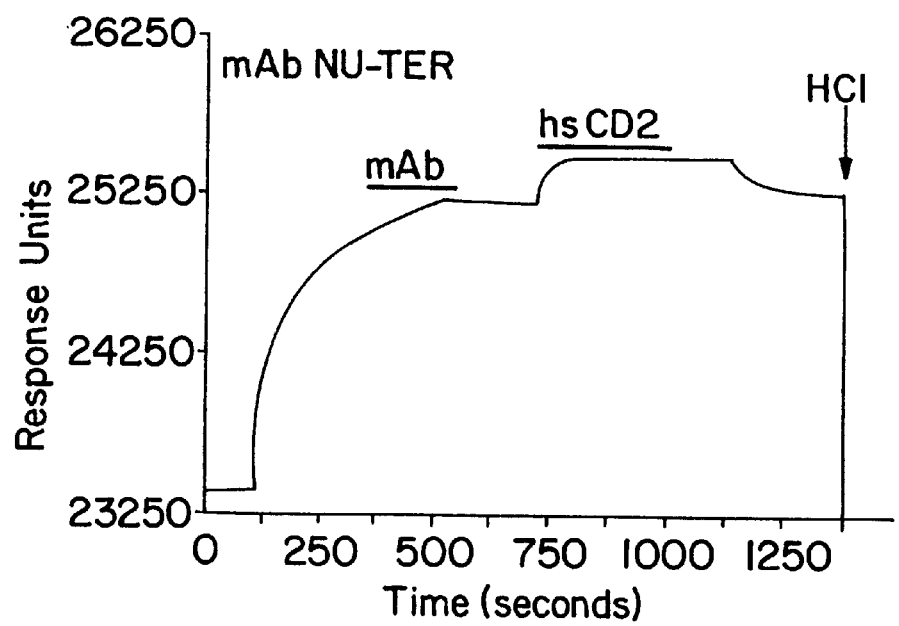
Figure 3H:
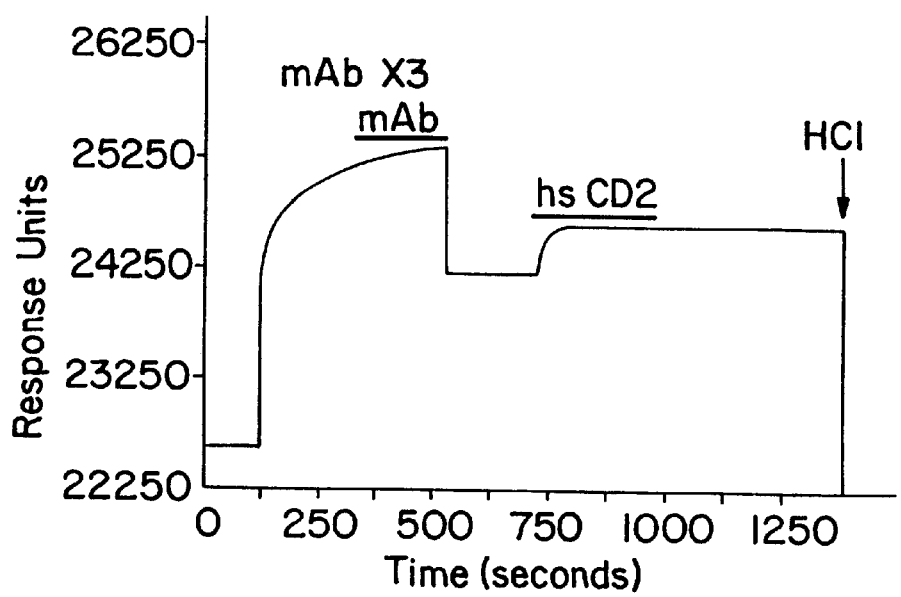

FIGS. 3A–3H show the binding of CD2 mAbs to untreated-hsCD2 (control) (FIGS. 3A–3D) and endo H-treated hsCD2 (FIGS. 3E–3H) on a BIAcore biosensor with Response Units, plotted on the y-axis against Time in Seconds on the X-axis. RAM-Fc was covalently coupled to the Dextran matrix (see Materials and Methods). The indicated monoclonal antibody (mAb) (tissue culture supernatant for X3; 1:100 dilution of ascites for the others) was injected for 7 min (1st bar) and subsequently 1 μg/ml of untreated (Control hsCD2) or endo H-treated hsCD2 (endo H hsCD2) was injected for 7 min (2nd bar). The flow-cell was then regenerated by eluting the bound proteins with 0.1 M HCl. The mAbs are: FIGS. 3A & 3E, mAb F92-3A11; FIGS. 3B & 3F, mAb 95-5-49; FIGS. 3C & 3G, mAb NU-TER; FIGS. 3D & 3H, mAb X3.

Figure 4A:
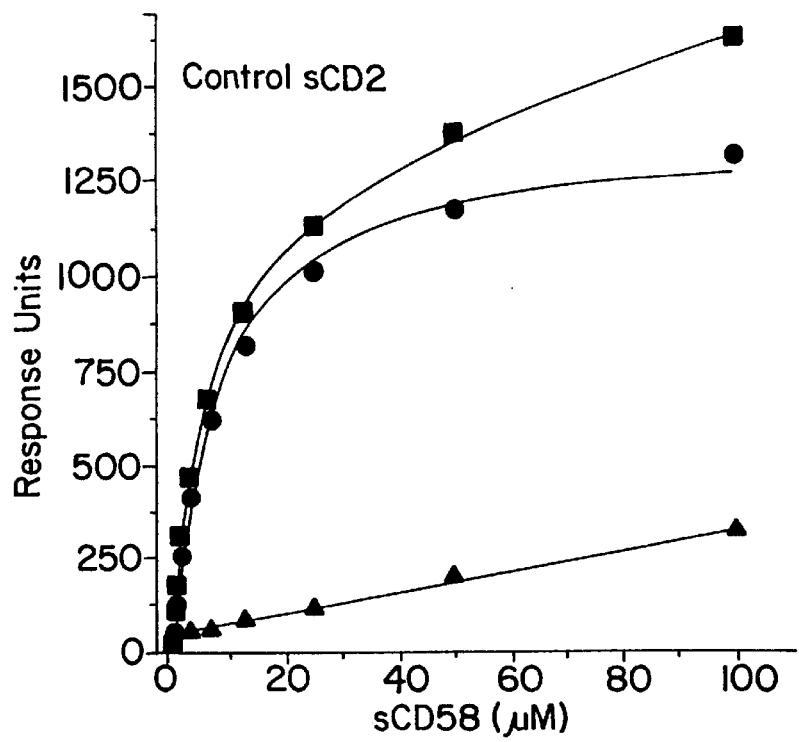
Figure 4B:
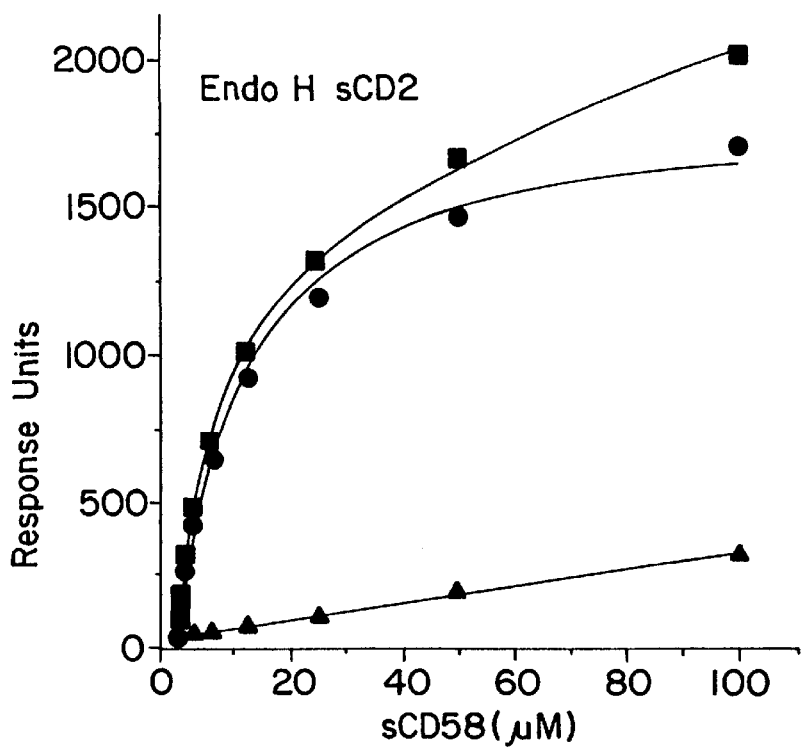
Figure 4A:
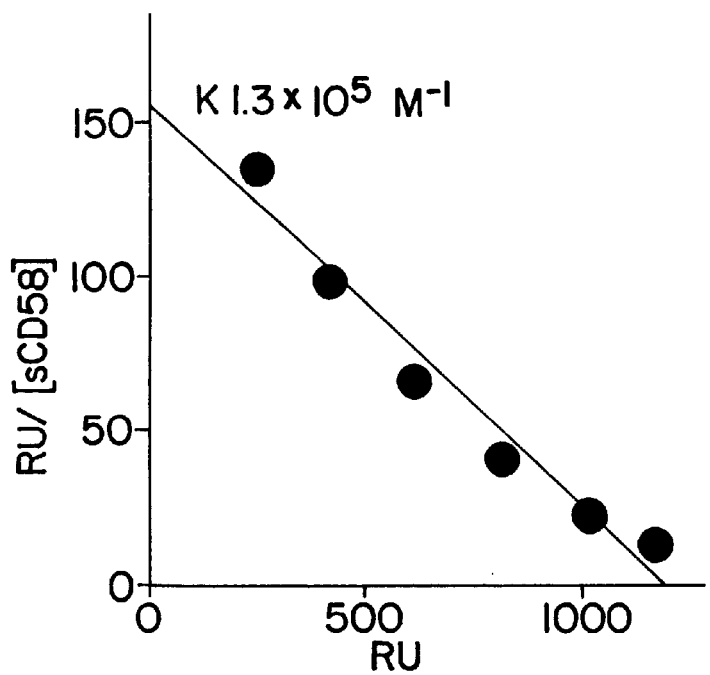
Figure 4B:
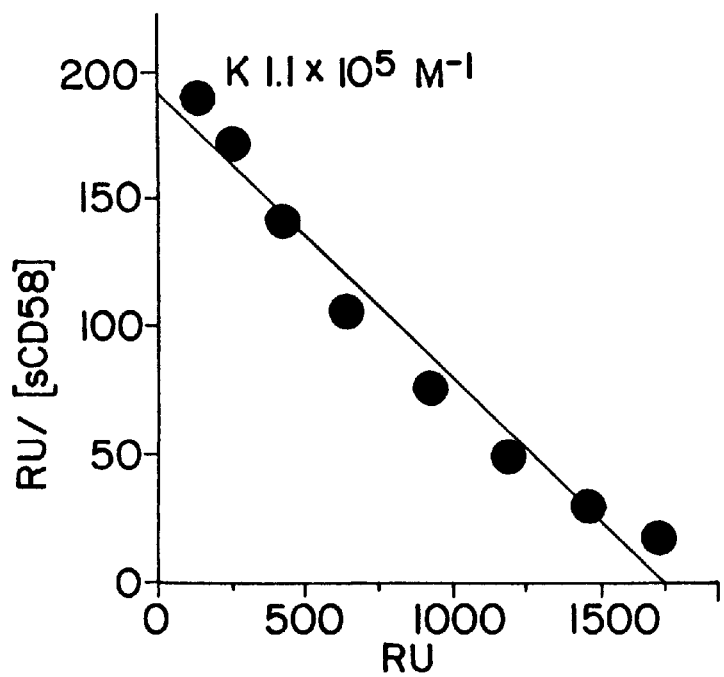

FIGS. 4A, 4B, 4A1, and 4B1 show the saturation binding of hsCD58 to untreated (FIG. 4A, control) and endo H-treated (FIG. 4B) hsCD2 on a BIAcore biosensor with Response Units plotted on the y-axis against concentration in μM of hsCD58 on the x-axis. Untreated-hsCD2 (FIG. 4A) and endo H-treated hsCD2 (FIG. 4B) were covalently immobilized to the Dextran matrix (see Materials and Methods) within different flow-cells and then increasing concentrations of hsCD58 were injected for 6 s through both CD2 flow-cells (squares) and a blank flow-cell (triangles, no protein immobilized). Specific binding (circles) was calculated as the differences between the responses in the CD2 and blank-flow cells. Insets: Scatchard plots of the specific binding. The Kd was determined by linear-regression analysis of the Scatchard plots as well as by non-linear curve fitting of the saturation binding curve. Both methods gave the same Kd values.

Figure 5A:
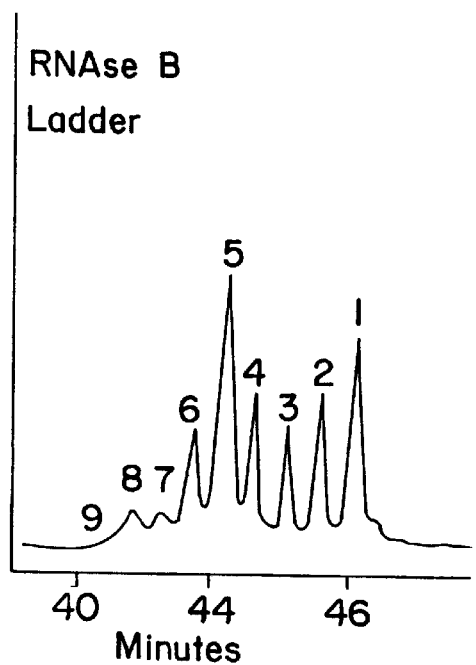
Figure 5B:
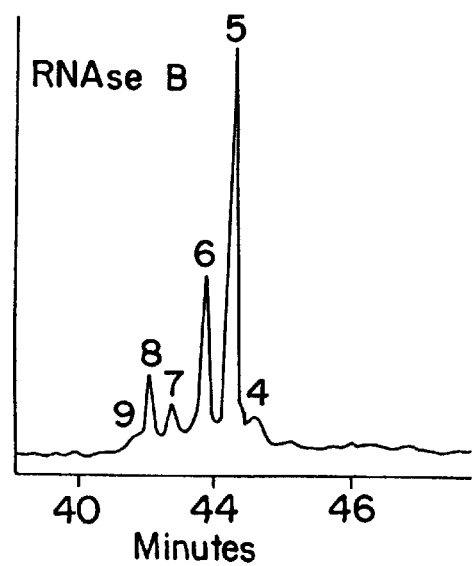
Figure 5C:
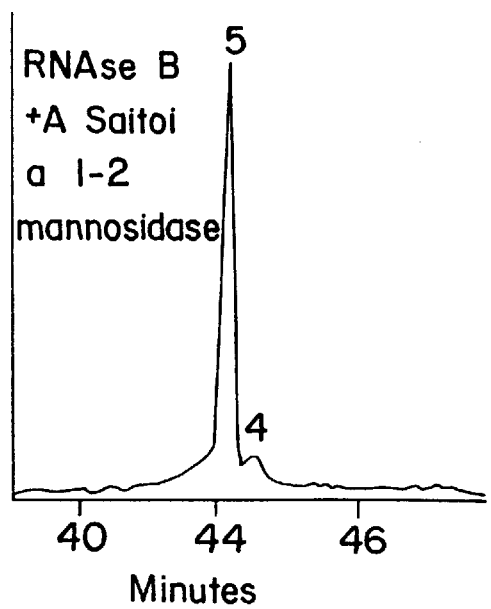
Figure 5D:
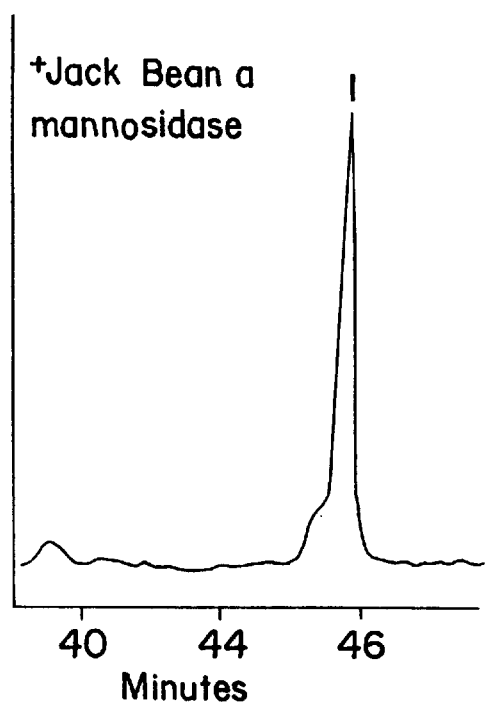
Figure 5E:
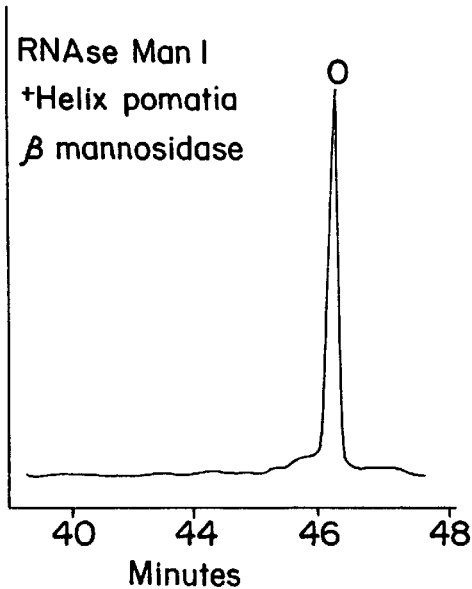
Figure 5F:
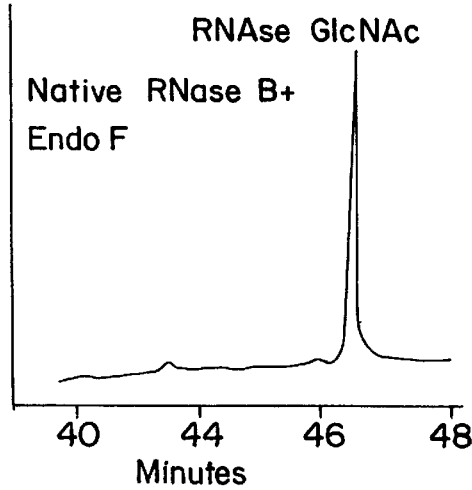
Figure 5G:
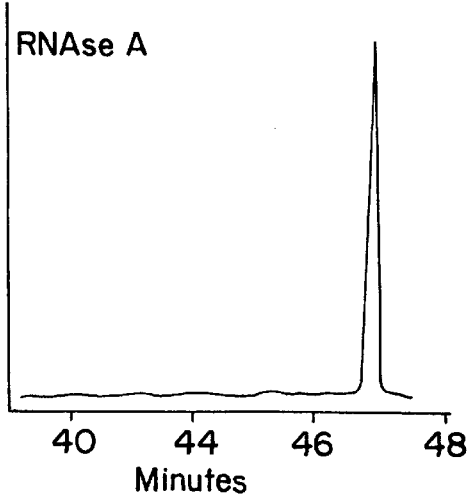
Figure 5H:
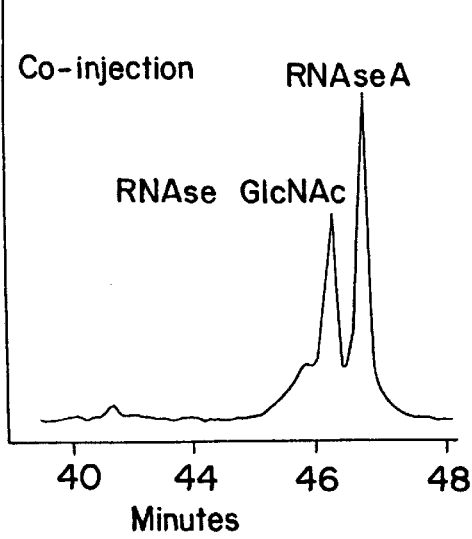

FIGS. 5A–5H show capillary electrophoretic (CE) analysis of glycoforms used for protease digestions in which Absorbance at 280 nm is plotted on the y-axis against minutes on the x-axis. FIG. 5A: the RNase B ladder used as CE standards. FIG. 5B: native RNase B. FIG. 5C: purified RNase B-Man$_5$ prepared by digesting RNase B with *A. saitoi* α(1–2)mannosidase. FIG. 5D: purified RNase B-Man$_1$ prepared by digesting RNase B with Jack Bean α-mannosidase. FIG. 5E: purified RNase B-Man0 prepared by digesting RNase-B-Man$_1$ with *H. pomatia* β-mannosidase. FIG. 5F: purified RNase B-GlcNAc prepared by digesting RNase B with endoglycosidase F. FIG. 5G: native RNase A. FIG. 5H: Co-injection of RNase B-GlcNAc and RNase A.

Figure 6A:
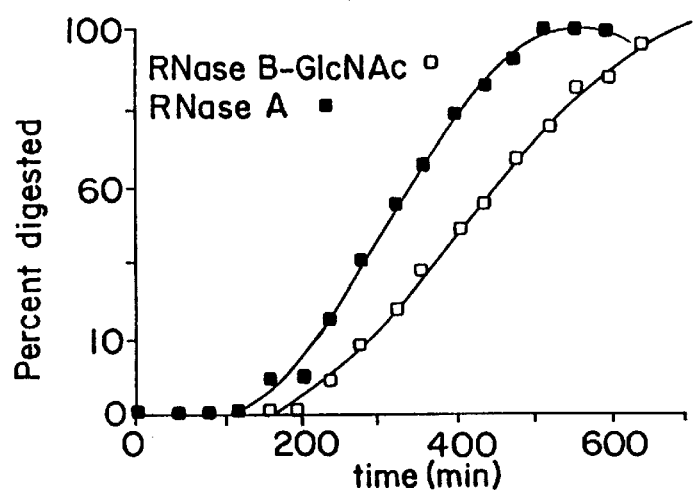
Figure 6B:
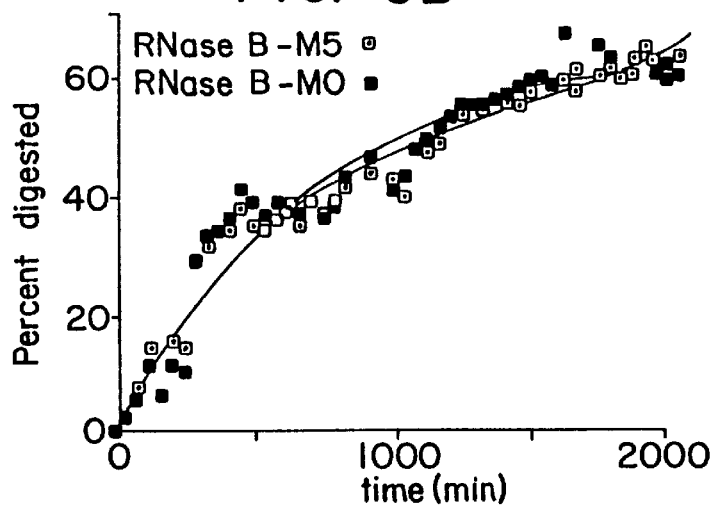
Figure 6C:
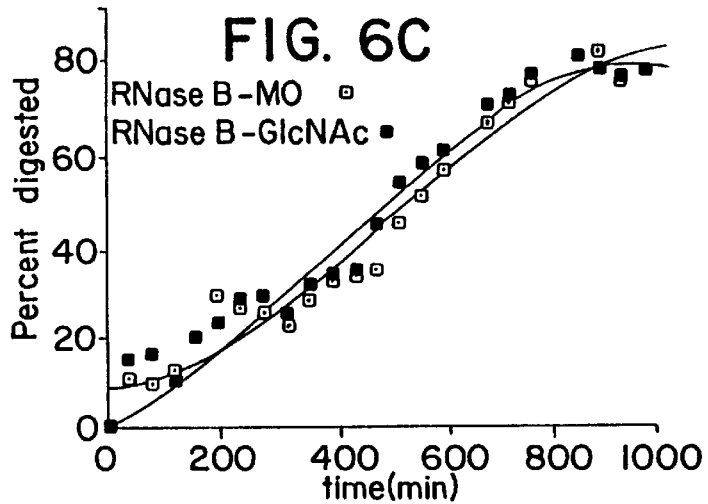

FIGS. 6A–6C show pronase digestions of different RNase B glycoforms and RNase A in which Percent Digested is plotted on the y-axis against time in minutes on the x-axis. Pronase digestions were carried out with RNAse A and RNAse B-GlcNAc (FIG. 6A) or RNAse B-Man$_5$ and RNAse B-Man$_0$ (FIG. 6B) or RNAse B-Man$_0$ and RNAse B-GlcNAc (FIG. 6C) in the capillary electrophoresis carousel at 37° C. Digestions were monitored continually by direct injection into the capillary immediately followed by electrophoresis.

Figure 7A:
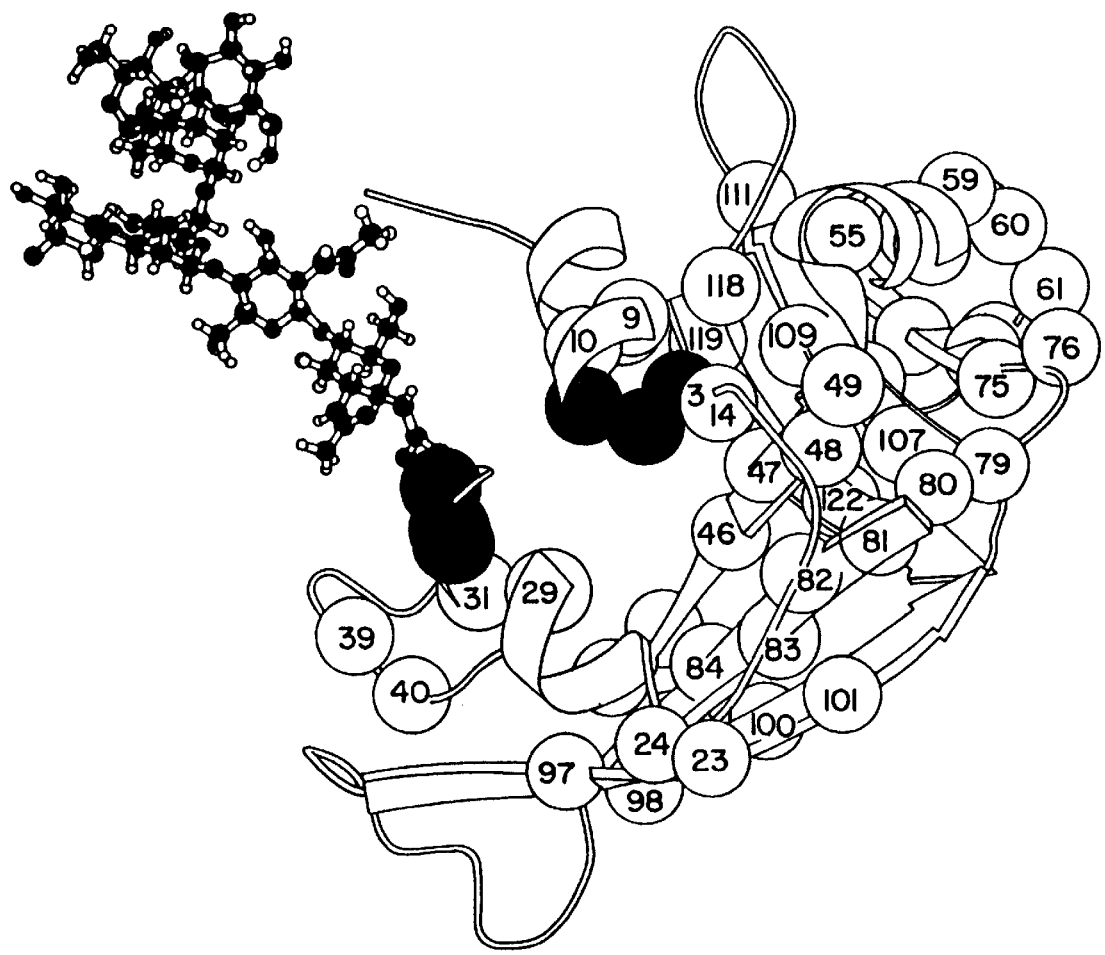

FIG. 7A. is a schematic representation of RNase highlighting those residues whose amide protons show modified hydrogen-deuterium exchange as a result of glycosylation of the enzyme at Asn34. The amide protons of RNase-GlcNAc, RNase Man$_1$, RNase Man$_5$ and RNase B Man$_5$ glycoforms, which show additional protection from solvent exchange when compared with RNase A, are represented by light-shaded circles, i.e. the protection is independent of the glycoforms. Those residues represented by dark circles are from amide protons and are glycoform dependent. They show additional protection from exchange in RNase Man$_1$ and RNase Man$_5$ glycoforms. In the case of the RNase GlcNAc glycoform, residues 10,11 and 12 in the active site are not protected from solvent exchange when compared with RNase A. However, 32, 34 and 35 (the other dark shaded circles) show the same behavior as the RNase Man$_1$ glycoform.

FIG. 7B is a graphic representation of amide proton-deuterium exchange data for selected residues of RNase glycoforms in the vicinity of the site of glycosylation. Time range in hours (h) is shown on the y axis for exchange of selected amide protons in Ribonuclease (RNase) glycoforms on the x axis. The data represent time ranges over which amide-proton resonances are observable during amide-proton/deuterium exchange for those residues represented by dark circles in FIG. 7A (which are glycoform dependent). The region of the bars in black corresponds to the time range in which the backbone amide-proton resonance is observable in the COSY analysis after initiation of the exchange process. During the following time range, represented by the white region of the bars, the amide-proton resonance exchanges out of the NMR spectrum. Key: (A) RNase A; (B) RNase B; (M5) RNase Man$_5$; (M1) RNase Man$_1$ and (G1) RNase GlcNAc.

FIG. 7C is a graphic representation of amide proton-deuterium exchange data for selected residues of RNase glycoforms both in the vicinity of and remote from the site of glycosylation (Asn 34). A comparison of amide-proton exchange rates (h$^{-1}$) is shown on the y axis for a number of residues(29, 31, 44, 48, 75, 79 and 85) indicated on the y axis. The decay in peak intensity with time of each NH—CαH resonance is monitored and the data fitted to an exponential decay curve to obtain the rate of solvent exchange. Correlation coefficients of >30.99 were obtained for the fit of the curve to the experimental data. The rates of amide-proton solvent exchange for these residues are similar in RNase B, RNase Man$_5$, RNase Man$_1$, and RNase GlcNAc, but are slower when compared to RNase A. For each residue the exchange rates for the five glycoforms (A) RNase A; (B) RNase B; (M5) RNase Man$_5$; (M1) RNase Man$_1$ and (Gi) RNase GlcNAc are shown.

In order to further illustrate the invention, the following detailed examples were carried out, although it will be understood that the invention is not-limited to these specific examples and the details described therein. References to show the state-of-the-art are indicated in parentheses and appended at the end.

A general method is used in these examples for engineering the glycosylation of proteins, using a glucosidase I inhibitor to render the sugars susceptible to the endoglycosidase enzyme, endo H. This enzyme cleaves N-linked oligomannose type glycans within the chitobiose core leaving a single N-acetylglucosamine residue attached to the protein. The glucosidase I inhibitor, N-butyldeoxynojirimycin, was added to cultures of non-mutant CHO cells secreting a soluble, recombinant form of human CD2 (hsCD2) which is normally glycosylated with predominantly endo H resistant oligosaccharides. In excess of 85% of the oligosaccharides of hsCD2 produced in these cultures were converted to endo H sensitive structures and the endo H-treated protein, after purification by antibody- and lectin-affinity chromatography, crystallized readily. The structure of this glycoprotein was determined to 2.8 Å resolution. Biosensor measurements showed that the binding of hsCD2 to monoclonal antibodies and its natural ligand, CD58 (LFA-3) is unaffected by truncation of the oligosaccharides to single GlcNAc residues following endo H treatment, in contrast to published studies of the properties of hsCD2 treated with peptide N-glycosidase F, which cleaves the N-glycosidic bond and therefore does not leave the single GlcNAc residue at the sequon. Protease-susceptibility analyses and nuclear magnetic resonance based dynamic stability studies of individual glycoforms of the model glycoprotein, bovine pancreatic RNAse, showed that the presence of a single N-linked GlcNAc residue endows the RNAse with essentially the same dynamic stability as Man$_5$GlcNAc$_2$ or larger oligosaccharides. These examples thus demonstrate that glucosidase I inhibitors can facilitate the structural analysis of glycoproteins.

EXAMPLE 1

In order to demonstrate the advantageous use of CHO cells for low levels of endomannosidase activity in the method of the invention, the oligosaccharide processing enzyme activity in these cells in culture was determined and compared with that determined with four other conventional cell lines, namely H9, Molt-4, K562 and HL60. These are well-known, widely distributed and readily available cell lines. For example, HL-60 cells are promyelocytic cells described by Collins et al., Nature 270, 347–349 (1977). They are also readily available from the American Type Culture Collection, Rockville, Md. under accession number ATCC CCL 240. K-562 cells are of myeloid origin described by Lozzio and Lozzio, Blood 45, 321–324 (1975). They are also readily available from the same depository under accession number ATCC CCL 243. MOLT-4 cells are lymphoid cells described in J. Nat'l. Cancer Inst. 49, 891–895 (1972). They are also readily available from the same depository under accession number ATCC CRL 1582. H9 cells are of lymphoid origin described by Gallo and Popovic, Science 224, 497–500 (1984). They are also readily available from the same depository under accession number ATCC HTB 176.

The enzyme assay and resulting activity are shown in the following Table 1. It was determined that the endomannosidase activity was less than 10% of the α-glucosidase activity in the cultured CHO cells.

TABLE 1

Determination of oligosaccharide processing enzyme activity in cultured cells

| Cell Line | endomannosidase $^{14}$C-glc released/mg | α-glucosidase $^{14}$C-glc-released/mg |
|---|---|---|
| H9 | 1076.1 | 697.8 |
| Molt 4 | 1052.5 | 861.3 |
| K562 | 500.0 | 655.2 |
| HL60 | 360.6 | 1073.5 |
| CHO | 84.9 | 903.6 |

Enzyme activities in detergent extracts from cultured cells were determined using a biosynthetically prepared radiolabelled substrate, [$^{14}$C-Glc]Glc$_3$Man$_9$GlcNAc$_2$, from bovine thyroid microsomes.

Endomannosidase assay: Cells were cultured in RPMI 1640 (Flow Laboratories, High Wycombe, Bucks, UK) supplemented with 10% foetal calf serum (Flow) and maintained in a humidified incubator at 37° C. with 5% $CO_2$ (Platt et al., 1992), and extracted with 100 mH MES (4-morpholineethanesulfonic acid) buffer, pH 6.5, containing 20 mM EDTA and 2% (v/v) Triton® X-100 non-ionic detergent for 30 min at 2° C. After centrifugation at 100,000×g, the supernatant extract was taken for enzyme determination. Extracts were incubated for 16 h at 37° C. in the presence of DNJ and EDTA to inhibit the hydrolysis by α-glucosidases and α-mannosidases, and the endomannosidase specific release of [$^{14}$C-Glc] $Glc_3Man_1$ was measured after separation by lectin-affinity chromatography.

α-Glucosidase assay: Extracts were incubated for 1 h at 37° C. and [$^{14}$C-Glc]$Glc_{1-3}$ was measured as described above.

EXAMPLE 2

Materials and Methods
Antibodies

The antibodies F92-3A11, 95-5-49 and NU-TER were obtained from Dr. Frances Gotch of the Institute of Molecular Medicine, John Radcliffe Hospital, Oxford, U. K., and are from the anti-CD2 antibody collection used for the third Leucocyte Typing Workshop (Bernard et al, 1987). The X3 antibody was a gift from Dr. David Y. Mason of the Department of Pathology and Bacteriology, John Radcliffe Hospital, Oxford. This antibody was used in the fourth Leucocyte Typing Workshop (Meuer, 1989).

Preparation of the construct encoding hsCD2

The polymerase chain reaction was used to produce DNA encoding hsCD2. The 5' oligonucleotide was complementary to the human CD2 leader sequence (Seed and Aruffo, 1987) and inserted, immediately upstream from the leader sequence, an Xba I site followed by 25 bp of the 5' untranslated sequence from the region immediately upstream of the initiating codon of the rat CD4 cDNA sequence (Clark et al., 1987). The sequence of this oligonucleotide was: 5'tagtagtctagatccccatccgctcaag-caggccaccatgagctttcca3' [SEQ ID NO:1]. The 3' oligonucleotide introduced a termination codon immediately after the codon for Lys-206 of the human CD2 cDNA (Seed and Aruffo, 1987; the numbering is as predicted for the unprocessed polypeptide), followed by a Bam HI site to facilitate subcloning. The sequence of this oligonucleotide was: 5'ctactaggatcctcatttctctggaca3' [SEQ ID NO:2]. The CD2 cDNA template used in the PCR reactions was obtained from Dr. David Wootton of Dr. Michael J. Owen's laboratory (Imperial Cancer Research Fund, Lincolns Inn Field, London, U.K.). The entire coding sequence of the PCR product was checked by dideoxy sequencing after subcloning into M13. The same approach was used for the expression of a soluble form of CD58(LFA-3).

Expression and purification of the hsCD2 and NB-DNJ treatment of cultures

For the expression of hsCD2, the Xba I-Bam H1 fragment was sub-cloned into the polylinker of pEE6.hcmv-GS (Bebbington and Hentschel, 1987; Davis et al., 1990). The expression construct (20 μg) was transfected with calcium phosphate into CHO-K1 cells and methionine sulfoximine-resistant clones were selected as described previously (Davis et al., 1990). To detect expression the conventional solid-phase, radioactive inhibition binding assay (Barclay and Ward, 1982) was used. This utilized human sCD2 domain 1 expressed as a fusion protein as described for rat CD2 domain 1 (Driscoll et al., 1991) adsorbed onto vinyl microtitre plates as a binding target and monitored inhibition of the binding of the anti-human CD2 mAb, X3 mAb to the plate; the bound mAb was detected with [$I^{125}$]-labelled rabbit anti-mouse F(ab'). For large scale production the highest-expressing cell line (line 2.14) was grown to confluence in cell factories (Nunc) and sodium butyrate was then added to a final concentration of 2 mM. The cultures were then left for a further 3–4 weeks prior to harvesting.

In initial optimization tests with NB-DNJ, 2×500 $cm^2$ flasks (Nunc) were seeded with line 2.14 cells in 75 ml glutamine-free medium GMEM-S (Gibco Ltd, Glasgow, U.K.) 10% Fetal Calf Serum (FCS) containing NB-DNJ at 0 mM, 0.5 mM, 1 mM, 1.5 mM or 2 mM. After 6 days 100 mls of CB2, 10% FCS containing sodium butyrate to give a final concentration of 2 mM and NB-DNJ at 0, 0.5 mM, 1 mM, 1.5 mM or 2 mM was added. Ten days after the addition of the butyrate, 0.5 ml samples of the supernatant were taken for comparison of secretion levels. The cultures were left for a total of 15 days before harvesting the supernatants. When large amounts of endo H treated hsCD2 were required for crystallization, the cells were grown to confluence in cell factories as described above and NB-DNJ was added with the sodium butyrate to a final concentration of 1.5 mM. These cultures were also left for a further 3–4 weeks prior to harvesting.

The hsCD2 was purified from the spent tissue culture medium, which had been pre-cleared by centrifugation at 10,000 g for 30 min., by affinity chromatography according to the methods of Arvieux and Williams (1988), using an antibody affinity column prepared with the X3 mAb, followed by gel filtration on SEPHACRYL® S-200 in 10 mM Hepes, 140 mM NaCl, pH 7.4.

Endo H digestions

For analysis of endo H sensitivity after preparation of the hsCD2 in the presence of various concentrations of NB-DNJ, 10 μg aliquots of the purified glycoproteins were incubated with 4, 20 or 100 mU/ml endo H-(Boehringer Mannheim) in 30 μl of 100 mM sodium acetate, pH 5.2. One unit (U) of endo H is the enzyme activity which hydrolyzes one micromole (μM) of dansyl-Asn-$(GlcNAc)_2$-$(Man)_5$ within one minute at 37° C., pH 5.5. After incubation overnight at 370 the digested samples were boiled in 1% SDS under reducing conditions prior to electrophoresis in 15% SDS-PAGE gels. For large-scale endo H treatment of hsCD2 for crystallization tests, 4 mgs of the purified glycoprotein was concentrated to 1–2 mg/ml in 0.1 M sodium acetate, pH 5.2, and then digested with 100 mU/ml endo H overnight at 370. To purify the endo H treated hsCD2 from the contaminating endo H-resistant fraction, the protein mixture protein was concentrated to 0.5 ml and then passed successively through a 5 ml SEPHADEX® G-50 column to remove free oligosaccharides and then through a 15 ml lectin affinity column consisting of equal parts of lentil lectin, concanavalin A and *Phaseolus vulgaris* lectin PHA-E, each coupled to SEPHAROSE® 4B or agarose (Sigma, E-Y Labs). The eluting protein was determined to be essentially free of contaminating hsCD2 bearing non-endo H sensitive oligosaccharides by SDS-PAGE on a 15% acrylamide gel. The fully endo H-sensitive protein was concentrated to 2 mls and then applied to SEPHADEX G-75 in 10 mM Hepes, 140 mM NaCl, pH 7.4 to remove free lectin eluting from the lectin-affinity column.

Production of crystals of endo H-treated hsCD2

The deglycosylated sCD2, in 10 mM Hepes, 140 mM NaCl, pH 7.4 was concentrated to 17 mg/ml and subjected to vapor-diffusion crystallization trials in sitting drops (Harlos, 1992) at room temperature. Initial trials were conducted using the Crystal Screen reagents (Hampton Research).

Biosensor analyses of the interaction of hsCD2 with CD2 mAbs and CD58(LFA-3)

The binding tests were performed on a BIAcore™ biosensor (Pharmacia Biosensor AB, Upsala, Sweden). RAM Fc was coupled to a CM5 sensor chip using the amine coupling kit (Pharmacia) as recommended (Karlsson et al., 1991). Human sCD2 and endo H-treated hsCD2 were coupled in the same way except that they were injected at 65 µg/ml and the HCl washing step was omitted. The buffer used was Hepes-buffered saline (HBS) which contains (in mM): NaCl 150, $MgCl_2$ 1, $CaCl_2$ 1, Na azide 10, 0.005% Surfactant P-20 (Pharmacia), and Hepes 10 (pH 7.4). Na azide was omitted during the coupling procedure. The mAb binding test (FIGS. 3A–3H) was performed at 37° C. with a buffer flow rate of 5 µl/min and RAM-Fc was regenerated with 0.1 M HCl. The hsCD58 binding test (FIGS. 4A–4B) was performed at 25° C. with a flow-rate of 20 µl/min.

NMR tests and measurement of amide proton exchange

Sample preparation and rate measurements (at 35° C. and pH 3.35) were carried out as previously described (Joao et al., 1992). The purity and structure of each glycoform studied was confirmed by capillary electrophoresis, mass spectrometry and by direct inspection of the NMR spectra.

Capillary Electrophoresis

This was carried out on a 72 cm fused silica capillary (ID=75 mm; Beckman P/ACE system with Gold™ Software) run at 300° C. in 20 mM sodium phosphate, 50 mM SDS, 5 mM sodium tetraborate, pH 7.2 at 1 kV for 1 min, 20 kV for 9 min after an injection time of 1.5 s.

Matrix assisted laser desorption mass spectrometry 150 pmols of glycoprotein and 275 nmoles of sinnapinic acid were co-crystallized on the target and the molecular weights obtained by the accumulation of data from ten shots from a UV laser (337 nm) using a Finnigan LASERMAT instrument with time of flight detection.

Preparation of RNase A and RNase B glycoforms

RNAse A and B (Sigma) were purified to capillary electrophoretic homogeneity by Concanavalin A SEPHAROSE affinity chromatography (Pharmacia) and SEPHADEX (G-50, Pharmacia) gel filtration chromatography. To generate homogeneous RNAse B-Man5, RNAse B was digested with A. saitoi α(1–2)mannosidase at an enzyme:substrate ratio of 25 mU:1 mg/ml in 50 mM sodium acetate, pH for 96 h at 370. Homogeneous RNAse B-GlcNAc was obtained by digesting 4 mg of RNAse B with 4 U of endo F in 40 ml of 20 mM phosphate, 50 mM EDTA, 0.02% azide and 50% glycerol, pH 7. RNAse B-Man1 was prepared by incubating RNase B with jack bean α-mannosidase at 5 U:1 mg/ml 10 mM sodium citrate, pH 4.5/0.2 mM Zn acetate at 30° C. RNAse B-Man0 was prepared by incubating the Man1 glycoform with *Helix pomatia* β1–4-mannosidase at an enzyme:substrate ratio of 1 U:5 mg at 37° C. in 100 mM sodium acetate, pH 4. All the reactions were continuously monitored by capillary electrophoresis. The RNAse B-Man5 and RNAse B-GlcNAc glycoforms were separated from both the released oligosaccharides and the glycosidases by HPLC gel permeation chromatography. All structures of all of the glycoforms were analyzed by CE, by co-injection with a RNase B standard glycoform ladder and with RNase A, and by matrix assisted laser desorption mass spectrometry. The RNase B standard ladder was prepared by mixing together partially digested samples from the enzyme digest described above to obtain the range of glycoforms from RNase B-Man9 to -Man0 and used as an internal standard to assign peaks.

Pronase digestions

In three separate tests, RNAse together with RNAse B-Man5 and RNase B-Man0 and RNAse B-GlcNAc were incubated with pronase in the capillary electrophoresis carousel at 37° C. In two complementary tests RNAse B-Man5 with RNase B-Man0 and RNase B-Man0 with RNAse B-GlcNAc were incubated together with pronase. In each case the enzyme to substrate ratio was 0.77 U:1 mg of RNAse in 50 mM Tris/HCl pH 7.5. Digestions were monitored continually by direct injection into the capillary and each incubation was repeated at least three times. The data, which determined the rate of cleavage of the intact glycoforms, were obtained by integration of the appropriate peaks.

RESULTS

A full-length cDNA clone encoding human CD2 (Seed and Aruffo, 1987) was truncated and mutated by polymerase chain reaction to encode a soluble form of CD2 (hsCD2) consisting of 182 residues with three potential glycosylation sites (Asn-89, Asn-141 and Asn-150) terminating at Lys-206 of the unprocessed translated product. This construct was then expressed in Chinese Hamster ovary (CHO-K1) cells using the glutamine synthetase-based gene expression system in which expression is driven by the human cytomegalovirus promoter and transfected clones are selected with the glutamine synthetase inhibitor methionine sulphoximine (Bebbington and Hentschel, 1987; Davis et al., 1990). Twenty-eight resistant clones were picked, the supernatants from 15 of which gave≧50% inhibition in the inhibition binding assay (Barclay and Ward, 1982). The best of these, line 2.14, expressed hsCD2 at a level of ~10 mg/liter under optimized growth conditions.

To determine the effect of NB-DNJ on the endo H-sensitivity of hsCD2 glycosylation, line 2.14 cells were cultured in the absence or in the presence of 0.5 mM, 1 mM, 1.5 mM or 2 mM NB-DNJ. Quantitative assays of the expression levels indicated that there was a three- to four-fold reduction in expression in the presence of 0.5–2 mM NB-DNJ. The hsCD2 expressed under these conditions was purified by monoclonal antibody X3 affinity chromatography followed by gel-filtration on SEPHADEX G-25. The glycoprotein was then digested with various concentrations of endo H (FIG. 1). With increasing NB-DNJ concentrations the resulting undigested hsCD2 migrated more slowly and as a tighter band on SDS-PAGE (FIG. 1), consistent with an increase in the size and uniformity of its glycosylation as oligosaccharide processing was progressively inhibited (Karlsson et al., 1993). The digestion of the 0.5 mM NB-DNJ-treated hsCD2 with limiting amounts of endo H produced three smaller products each differing by 2–3 kD (FIG. 1, lane 6). It is believed that these correspond to hsCD2 forms bearing two, one or no oligosaccharides, suggesting that all three potential glycosylation sites are utilized. There was a concomitant increase in sensitivity to endo H with increasing NB-DNJ concentrations. However, at the two highest NB-DNJ concentrations there was little difference in the endo H sensitivity, suggesting that inhibition of glucosidase I is complete at an NB-DNJ concentration of 1.5 mM. Densitometric analysis of the gel indicated that at the highest concentration of NB-DNJ approximately 15% of the hsCD2 remained endo H resistant, suggesting that a relatively inefficient glucosidase I by-pass mechanism exists in these cells.

The endo H sensitivity of hsCD2 expressed in the presence of NB-DNJ suggested that the protein could be prepared essentially free of glycosylation for structural and functional studies. Four milligrams of hsCD2 was prepared in the presence of 1.5 mM NB-DNJ and treated with endo H. Lectin-depletion tests indicated that the endo H-resistant contaminants consisted of a variety of glycoforms that bound to either concanavalin A, or lentil lectin. An affinity column composed of equal parts of these lectins coupled to SEPHAROSE 4B and *Phaseolus vulgaris* lectin PHA-E bound to agarose proved effective in removing the contaminants (FIG. 2A, lane 4). Matrix assisted, laser desorption mass spectrometry indicated that the molecular weight of the endo H treated lectin-affinity purified hsCD2 is 21555 Da, a value which agrees well with the calculated MW of 21575 for the hsCD2 polypeptide with single GlcNAc residues at each of three N-glycosylation sites (FIG. 2B). In crystallization trials this protein formed high quality crystals with dimensions of 0.5×0.1×0.1 mm which diffract to Bragg spacings of 2.5 Å. The crystal structure of hsCD2 has been completed to 2.8 Å resolution.

A recent study of a truncated form of hsCD2 suggested that the complete removal of the N-linked oligosaccharide of domain 1 with peptide N-glycosidase F eliminated the binding of antibodies and the natural ligand, CD58 (LFA-3), to CD2, suggesting that the structure of the molecule is disrupted by deglycosylation (Recny et al., 1992). Because it is essential that structure determinations be biologically relevant, the binding of NB-DNJ/endo H-treated hsCD2 to anti-CD2 mAbs and the natural CD2 ligand CD58 (LFA-3) was analyzed using a BIAcore™ biosensor. This instrument uses an optical method to detect binding of macromolecules to ligands immobilized on a Dextran matrix within a small flow-cell.

In order to compare the binding of the two hsCD2 preparations to several mAbs (F92-3A11, 95-5-49, NU-TER and X3), an affinity-purified rat anti-mouse Fc antibody (RAM-Fc) was first covalently immobilized onto the sensor surface and then used repeatedly following regeneration with 0.1 M HCl (FIGS. 3A–3H), arrows). In each test the mAb, in ascites fluid or tissue culture supernatant (TCS), was first injected through the flowcell for 7 min (FIGS. 3A–3H) during which time it bound the immobilized RAM-Fc as shown by the increase in response units (RU, 1 RU is equivalent to approximately 1 pg of protein). Following mAb binding either untreated hsCD2 (FIGS. 3A–3D)) or endo H-treated hsCD2 (FIGS. 3E–3H) was injected for 7 min. For each of 4 mAb tested there was binding to both forms of hsCD2 and in each case the extent of binding and the rate of dissociation of the bound CD2 were similar.

The affinity of untreated and endo H-treated hsCD2 for a soluble form of the natural CD2 ligand, hsCD58, was analyzed as before for rat sCD2 binding to its natural ligand rat CD48 (van der Merwe et al., 1993a,b). Untreated hsCD2 (FIG. 4A) and endo H-treated hsCD2 (FIG. 4B) were covalently immobilized to the Dextran matrix in different flowcells. Increasing concentrations of hsCD58 were then injected through both flow-cells as well as a control flow-cell (with nothing immobilized) and the equilibrium binding levels were determined (FIGS. 4A–4B). Since the injection of high concentrations of protein in itself leads to an increase in the response, specific binding was calculated as the difference between the response observed in the CD2- and the blank-flowcells (FIGS. 4A–4B). The dissociation constant was determined from Scatchard plots of the data (FIGS. 4A–4B, insets). These results demonstrate that hsCD58 binds untreated- and endo H-treated hsCD2 with a similar affinity (Kd 8 and 9 µM, respectively).

It has thus far not been possible to generate a sufficiently pure peptide N-glycosidase F-treated form of hsCD2 that would allow a detailed analysis of the structural and functional properties of fully deglycosylated hsCD2 analogous to that prepared by Recny et al. (1992). In order to determine the structural implications of truncating oligosaccharides to single GlcNAc residues, the model glycoprotein ribonuclease (RNase) was studied by protease digestion and NMR methods. Individual RNase glycoforms were prepared by endo- and exo-glycosidase digestion and characterized by capillary electrophoresis (FIGS. 5A–5H); the structures were confirmed by coinjection with the RNase standard glycoform ladder.

The results of the pronase digestions of a mixture of RNase B-GlcNAc with RNase A (FIG. 6) show that the glycosylated form-of the molecule is relatively protected from the protease. The time taken for 50% of RNase B-GlcNAc to be cleaved was approximately 25% longer than for RNase A, which is unglycosylated. Digestions of RNase B-Man5 with RNase B-Man0 and of RNase B-Man0 with RNase B-GlcNAc (FIG. 6) showed that the resistance of the three glycoforms to pronase was the same regardless of the size of the attached oligosaccharide.

The rates of exchange of labile hydrogens in proteins and the hydrogen of bulk water allow insights into the conformational and dynamic properties of proteins (discussed by Joao et al., 1992). In comparisons of unglycosylated RNase A and fully glycosylated RNase B the exchange of amide protons with solvent ($D_2O$) has been shown to be markedly affected by the presence of the oligosaccharides, implying that glycosylation enhances the global dynamic stability of the enzyme (Joao et al., 1992). In the present work the NH-ND exchange rates for the individual amino acid residues in RNase A were compared with RNase B, RNAse-Man5, RNase-Man1 and RNase-GlcNAc. Amide protons at the majority of residues distributed throughout the molecule were protected from exchange to similar extents in each of the glycosylated molecules regardless of the extent of glycosylation (FIG. 7A). Only for residues 10, 11 and 12 were exchange rates for the glycoform containing a single GlcNAc residue similar to the rates observed for the RNase A (FIGS. 7B and 7C). This result suggests that the global dynamic stability of the enzyme is enhanced to similar extents by full-length and truncated oligosaccharides consisting of single GlcNAc residues.

In toto, this work demonstrates that glucosidase I inhibitors such as NB-DNJ and the like can facilitate the structural analysis of glycoproteins and suggests that the dynamics, protease resistance and structure of the endo H-treated glycoproteins thereby derived may be the same as the fully glycosylated glycoforms.

Various other examples will be apparent to the person skilled in the art after reading the present disclosure without departing from the spirit and scope of the invention. All such other examples are meant to be included within the scope of the appended claims.

REFERENCES (1) Arvieux, J. and Williams, A. F. (1988) in *Antibodies: A Practical Approach*, Ch. 5pp. 113–136, IRL Press, Oxford.

(2) Barclay, A. N; and Ward, H. A. (1982) *Eur. J. Biochem.* 129, 447–458.

(3) Bebbington, C. R. and Hentschel, C. C. G. (1987) in *DNA Cloning; A Practical Approach*, (Glover, D. M., ed), Vol III, pp. 163–188, IRL Press, Oxford.

(4) Bernard, A., Brown, M. H., Yang, S. Y. and Wallace, D. L. (1987) in "Leucocyte Typing III: White Cell Differentiation Antigens" (A. J. McMichael, Ed.) Oxford University Press, p. 106.

(5) Clark, S. J., Jefferies, W. A., Barclay, A. N., Gagnon, J. and Williams, A. F. (1987) *Proc. Natl Acad. Sci. USA* 84, 1649–1653.

(6) Davis, S. J. Puklavec, M. J., Ashford, D. A., Harlos, K., Jones, E. Y., Stuart, D. I. and Williams, A. F. (1993) *Prot. Eng.* 6,229–232.
(7) Davis, S. J., Ward, H. A., Puklavec, M. J., Willis, A. C., Williams, A. F. and Barclay, A. N. (1990) *J. Biol. Chem.* 265, 10410–10418.
(8) Driscoll, P. C., Cyster, J. G., Campbell, I. D. and Williams, A. F. (1991) *Nature* 353, 762–765.
(9) Harlos, K. (1992) *J. Appl. Crystallogr.* 25, 536–538.
(10) Hiraizumi, S., Spohr, U. and Spiro, R. G. (1993) *J. Biol. Chem.* 268, 9927–9935.
(11) Joao, H. C. and Dwek, R. A., *Eur. J. Biochem.* 218, 239–244 (1993).
(12) Joao, H. C., Scragg, I. G. and Dwek, R. A. (1992) *FEBS Lett.* 307, 343–346.
(13) Jones, E. Y., Davis, S. J., Williams, A. F., Harlos, K. and Stuart, D. I. (1992) *Nature* 360, 232–239.
(14) Karlsson, G. B., Butters, T. D., Dwek, R. A. and Platt, F. M. (1993) *J. Biol. Chem.* 268, 570–576.
(15) Karlsson, R., Michaelsson, A. and Mattsson, L. (1991) *J. Immunol. Methods* 145, 229–240.
(16) Meur, S.C. (1989) in "Leucocyte Typing IV: While Cell Differentiation Antigens" (Knapp, W., Dorken, B., Gilks, W. R., Rieber, E. P., Schmidt, R. E., Stein, H. and A. E. G. Kr. von dem Borne, Eds) Oxford University Press p. 270–272.
(17) Platt, F. M., Karlsson, G. B. and Jacob, G. S., (1992) *Eur. J. Biochem.* 208, 187–193.
(18) Recny, M. A., Luther, M. A., Knoppers, M. H., Neidhardt, E. A., Khandekar, S. S., Concino, M. F., Schimke, P. A., Francic, M. A., Moebius, U., Reinhold, B. B., Reinhold, V. N. and Reinherz, E. L. (1992) *J. Biol. Chem.* 267, 22428–22434.
(19) Seed, B. and Aruffo, A. (1987) *Proc. Natl. Acad. Sci. USA* 84, 3365–3369.
(20) Stanley, P. (1989 *Mol. Cell. Biol.* 9, 377–383.
(21) van der Merwe, P. A., Brown, M. H., Davis, S. J. and Barclay, A. N. (1993) *EMBO J.* 12, 4945–4954.
(22) van der Merwe, P. A., McPherson, D. C., Brown, M. H., Barclay, A. N., Cyster, J. G., Williams, A. F., and Davis, S. J. (1993) *Eur. J. Immunol.* 23, 1373–1377.

What is claimed is:

1. A method for modifying the carbohydrate moiety on glycoproteins comprising:

(a) treating glycoprotein-secreting CHO cells having low endomannosidase activity under cell maintenance conditions with N-butyl deoxynojirimycin under non-denaturing conditions;

(b) secreting and purifying the glycoprotein from the cells of step (a); and (c) treating the secreted and purified glycoprotein from step (b) with endoglycosidase H under non-denaturing conditions to provide a glycoprotein with a single GlcNAc residue at each glycosylation sequon, thereby facilitating the structural and functional analysis of said secreted and purified glycoprotein.

2. The method of claim 1 in which the N-butyl deoxynojirimycin concentration is at least about 100 μM.

3. The method of claim 2 in which the endoglycosidase H concentration is from about 4 to about 100 mU/ml.

* * * * *

SEQUENCE LISTING

```
(1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:1:

TAGTAGTCTA GATCCCCATC CGCTCAAGCA GGCCACCATG AGCTTTCCA          49

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:2:

CTACTAGGAT CCTCATTTCT CTGGACA                                  27
```